United States Patent [19]

Ch'ing-Lung

[11] Patent Number: 4,628,169
[45] Date of Patent: Dec. 9, 1986

[54] MINI ELECTRICAL SYRINGE NEEDLE DESTROYER

[76] Inventor: Hsieh Ch'ing-Lung, 113, 5th F., Section 5, Yen-Ping N. Road, Taipei, Taiwan

[21] Appl. No.: 552,324

[22] Filed: Nov. 16, 1983

[51] Int. Cl.4 .................. B23H 9/00; H05B 3/00
[52] U.S. Cl. ........................... 219/68; 83/15; 83/580; 128/303.1
[58] Field of Search ............. 83/15, 16, 580; 219/68, 219/69 W, 69 R, 69 M, 383, 384, 70; 128/303.1, 303.13, 303.14, 303.18, 303.19; 29/402.06, 402.08, 403.4

[56] References Cited

U.S. PATENT DOCUMENTS

| | | | |
|---|---|---|---|
| 1,502,932 | 7/1924 | Young | 219/231 |
| 2,606,266 | 8/1952 | Duch et al. | 219/68 |
| 3,091,145 | 5/1963 | Manganelli | 83/580 |
| 3,469,750 | 9/1969 | Vanderbeck | 83/580 |
| 3,683,733 | 8/1972 | Johan et al. | 83/580 |
| 3,851,555 | 12/1974 | Eldridge et al. | 83/580 |
| 4,040,425 | 8/1977 | Goodling et al. | 219/384 |
| 4,255,996 | 3/1981 | Choksi et al. | 83/580 |
| 4,275,628 | 6/1981 | Greenhouse | 83/580 |
| 4,315,448 | 2/1982 | Ball | 83/580 |
| 4,404,881 | 9/1983 | Hanifl | 83/580 |
| 4,447,694 | 5/1984 | Brochier et al. | 219/68 |
| 4,531,437 | 7/1985 | Szablak et al. | 83/580 |

FOREIGN PATENT DOCUMENTS 2732770 2/1979 Fed. Rep. of Germany .... 83/926 B

Primary Examiner—A. D. Pellinen
Assistant Examiner—Geoffrey S. Evans
Attorney, Agent, or Firm—Holman & Stern

[57] ABSTRACT

A mini electrical syringe needle destroyer, consisting of a syringe needle destroyer, a neighboring needle detaching device contained in the same framework as the destroyer, and a needle collecting box that can be plugged into the framework for automatic collection of waste needles.

1 Claim, 5 Drawing Figures

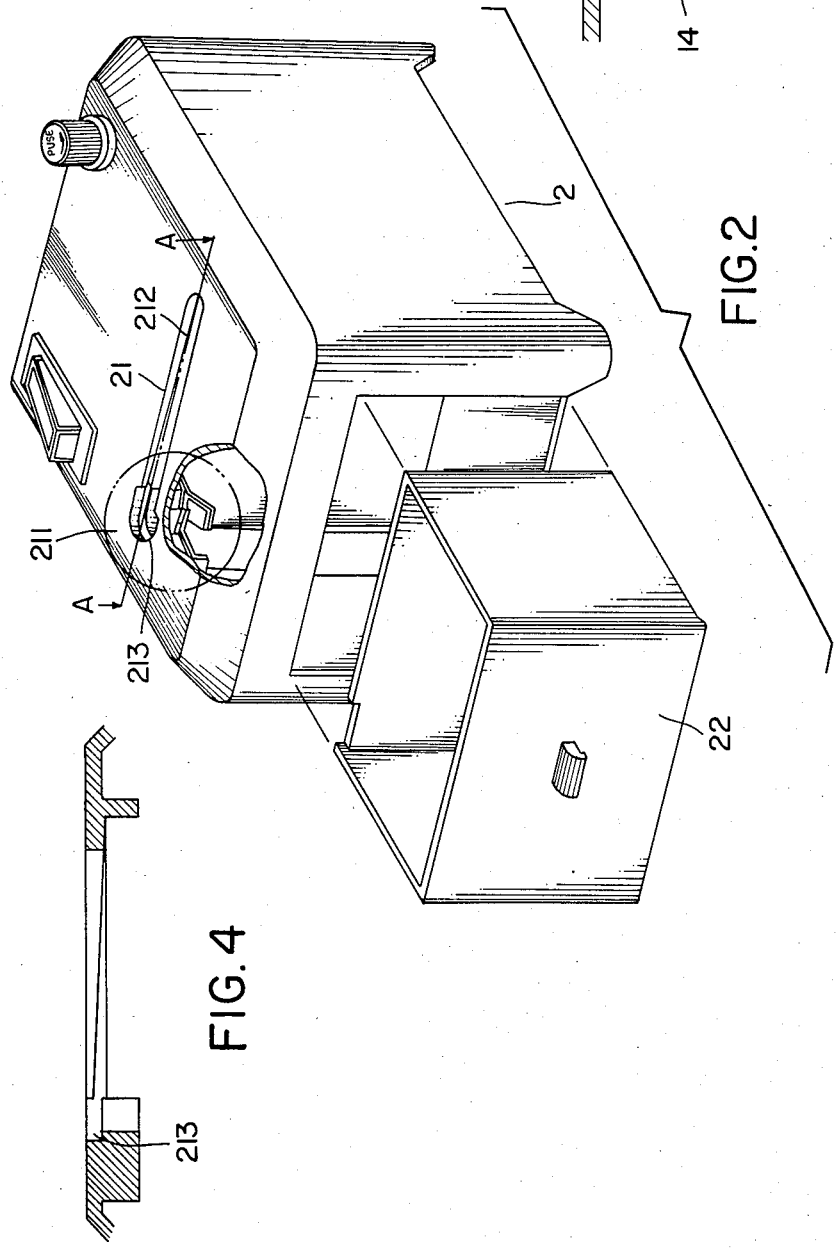
FIG. 2
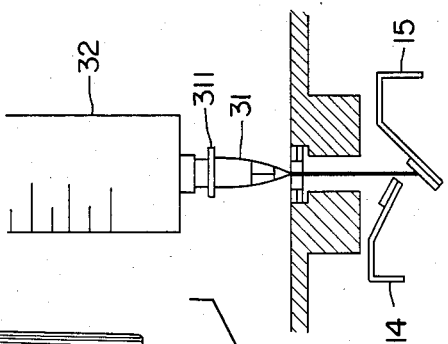
FIG. 3
FIG. 4

4,628,169

MINI ELECTRICAL SYRINGE NEEDLE DESTROYER

BACKGROUND OF THE INVENTION

Usually hospital people either throw away used syringe needles or sterilize them and reuse them. In case that these needles are thrown away, infections may be spread out and may endanger (carelessly hurt human bodies and cause infections) cleaners' health. If these needles are reused, they may hurt medical people and cause infections in the process of detaching, sterilizing and storing these needles. For security considerations, basically all medical people usually throw away their needles. In view of this, this invention is made to provide a mini electrical syringe needle destroyer.

SUMMARY OF THE INVENTION

The major object of this invention is to provide a mini electric syringe needle destroyer with a power control switch, a circuit protecting device (fuse), a transformer, and two inter-crossing, non-contacting electrodes which can bring about flash electric-heat to destroy syringe needles.

Another object of this invention is to provide a mini electric syringe needle destroyer with a needle detaching device which consists of a round needle-head inserting hole located on top of the outer case, i.e., on top of two non-contacting electrodes of the needle destroying device, and a needle detaching slide track with its upper end connecting to the needle-head inserting hole, of which the width is between the neck of the injector and the shoulder of the needle-head.

The major advantage of this invention is that the user simply holds the injector and plugs the used needle head into the needle-head destroy device so that the needle is in contact with both non-contacting electrodes. At this moment the used needle will absorb the strong current resulting from flash short-circuit of the two electrodes.

The second advantage of this invention is that the destruction, the detachment, and the collection of the needles can be done all at once, thus simplifying the operation.

BRIEF DESCRIPTION OF THE DRAWINGS

FIG. 2 is an exploded perspective view of the device part broken away, FIG. 3 is a sectional view through part of the device showing a needle inserted for destruction, FIG. 4 is an enlarged sectional view on line A—A of FIG. 2.

DESCRIPTION OF THE PREFERRED EMBODIMENT

Figure 1:
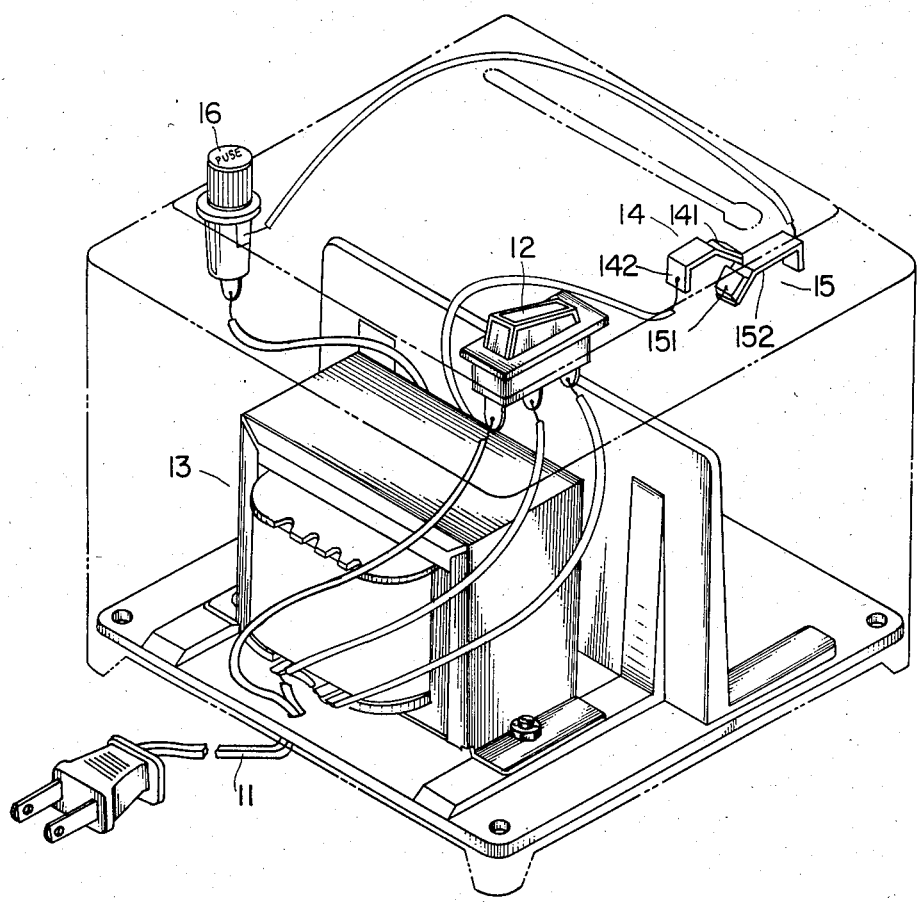
FIG. 1 is a perspective view of a needle-head destroy device in accordance with the invention, with its outer casing shown in phantom.
Figure 5:
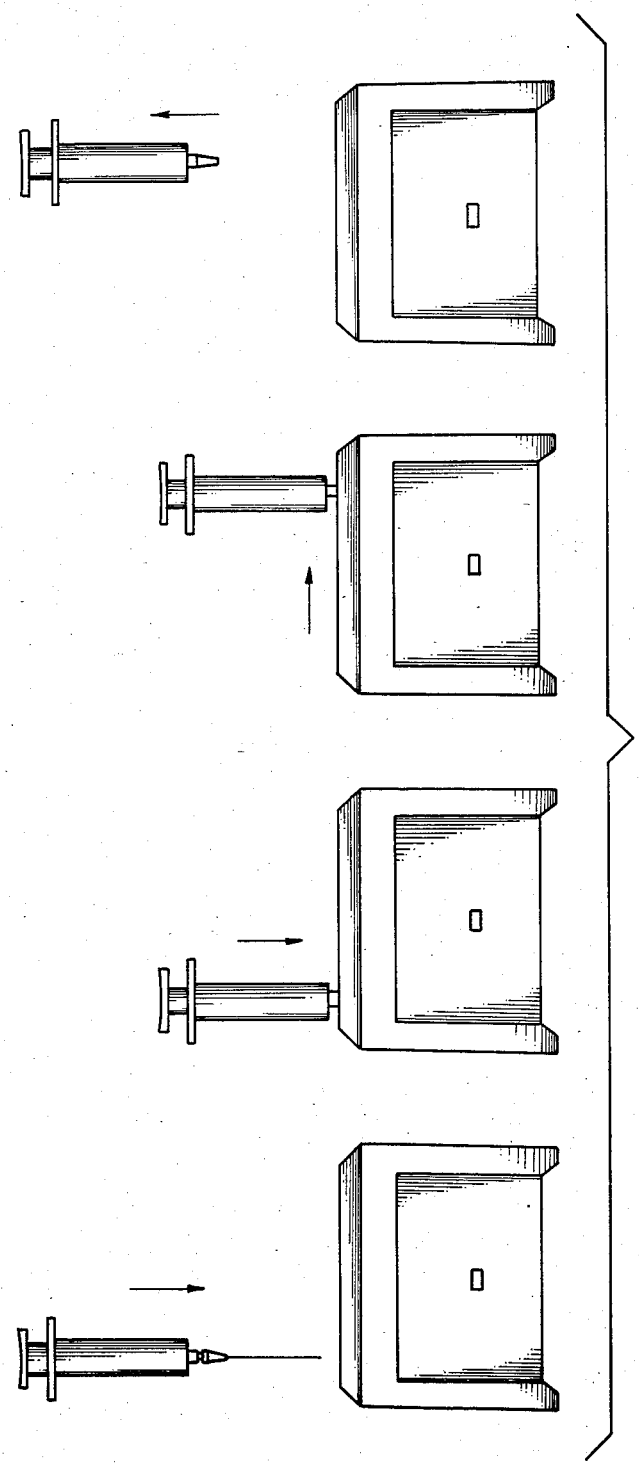
FIG. 5 is a diagram showing the sequence steps in the destruction of a needle.

Please refer to FIG. 1 and FIG. 2. FIG. 1 is a better illustration of actual use of the syringe needle-head destroy device, while FIG. 2 is the overall system configuration. This invention consists of the needle-head destroy device shown in FIG. 1, the outer case shown in FIG. 2, and the needle-head collecting box within the case. The needle-head destroy device consists of the power wires 11 that fit home-use power supply (110 V or 220 V), a switch 12, a transformer 13, two electrodes 14, 15 and fuse 16. The electrodes 14 and 15 are, respectively, high-melting point platinum-coated 141, 151, and alloy of copper and gold inner-layer 142, 152. As shown in FIG. 2, there is a keyhole-shaped needle-head detaching device 21 on top of the outer case. The needle-head detaching device 21 includes a needle-head inserting hole 211 and a needle-head slide track 212 with inclined sides (See FIG. 4). The needle-head inserting hole 211 is a round hole on top of the two electrodes 14 and 15 so that when needle-heads are inserted they will cause a downward pressure on the electrodes. A hoof-shaped supporting frame is located under the said hole, somewhat lower than the needle-head slide track 212, and with the same width as that of the needle-head slide track. The hoof-shaped supporting frame 213 has a width as large as that of the needle-head slide track 212, but a little smaller than the needle-head shoulder 311, and larger than the rest of needle-head. The drawer like needle-head collector 22 is equipped with a heat-insulating metal plate.

The operations proceed as follows:

(1) First press down the switch connector 12 for power supply.

(2) After heated, insert the needle-head 31 into the needle-head insertion hole 211. Then the needle-head 31 forms a short circuit between electrodes 14 and 15. As the cross section of the needle-head is very small, and its electric resistance is larger than the electrodes (Electric resistance reversely proportionates with the cross section.), the needle-head can completely absorb the strong current resulting from the flash of short circuit. The needle-head 31 will thus be melted and deformed by the high temperature enabling the injector to move downward until the needle-head flange 311 is stuck by supporting frame 213.

(3) Then the injector and the needle-head can be moved along to the other side of the needle-head slide track 212. Since the supporting frame 213 is a little lower than the needle-head slide track 212, the flange of the needle-head, 311, will be stuck under the needle-head slide track.

(4) Hence in the sliding process the needle-head that could be destroyed at any time is separated from the injector 32 by the inclined guide track walls and drops on a metal plate (not shown) in the needle-head collecting box 22 and completes destroying, detaching, and needle-head collecting safely. Since transformer 13 decreases several times the input voltage such that the voltage across the electrodes is only 3–4 voltages, limiting the fuse (16) current between a safe range of 5–30 Amp. The operating procedures are shown in FIGS. 1, 2, 3 and 4. In the illustrated example, the fuse (16) current is 5–30 Amp. When accidental short-circuit on the electrodes 14 and 15 is incurred by any accidental objects, the fuse will be burned up to cut off power and prevent any extension of danger.

The invention covers any device that modifies or changes the detailed structure, configuration, or operation described herein without leaving the spirit and limit of this invention.

What is claimed is:

1. A destruction device for a flanged needle head attached to a syringe, the device including a casing having a top wall provided with a needle head insertion opening, electric circuit means associated with the casing including a pair of electrodes within the casing under the needle head insertion opening, the electrodes being mutually located for receiving a needle portion of a needle head inserted in the opening therebetween whereby a short circuit is created between the electrodes for melting the needle portion, and the casing further including separator means for disconnecting the needle head with melted needle portion from the syringe, and collector means into which the separated needle head falls, wherein the separator means comprises an elongate guide track in the top wall of the casing extending from the needle head insertion opening, the guide track having downwardly inclined side walls for receiving the needle head flange thereunder after melting of the needle portion whereby sliding of the needle head along the guide track effects separation of the needle head from the syringe.

* * * * *